US010196675B2

(12) United States Patent
James et al.

(10) Patent No.: US 10,196,675 B2
(45) Date of Patent: *Feb. 5, 2019

(54) SOLID MEDIUM FOR THE STORAGE OF BIOLOGICAL MATERIAL

(71) Applicant: GE Healthcare UK Limited, Little Chalfont (GB)

(72) Inventors: Martin D. James, Cardiff (GB); Jeffrey K. Horton, Cardiff (GB); Peter J. Tatnell, Cardiff (GB)

(73) Assignee: GE Healthcare UK Limited, Little Chalfont (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/175,478

(22) Filed: Jun. 7, 2016

(65) Prior Publication Data

US 2016/0273024 A1   Sep. 22, 2016

Related U.S. Application Data

(63) Continuation of application No. 13/798,483, filed on Mar. 13, 2013, now Pat. No. 9,365,890.

(30) Foreign Application Priority Data

Jan. 30, 2013 (GB) .................................. 1301618.3

(51) Int. Cl.
*C12Q 1/00* (2006.01)
*C12Q 1/6806* (2018.01)
(Continued)

(52) U.S. Cl.
CPC ......... *C12Q 1/6806* (2013.01); *A01N 1/0215* (2013.01); *C12N 9/22* (2013.01);
(Continued)

(58) Field of Classification Search
CPC .................................................. C12Q 1/6806
(Continued)

(56) References Cited

U.S. PATENT DOCUMENTS 5,739,005 A   4/1998 Rodriguez-Kabana
5,820,998 A   10/1998 Hotaling et al.
(Continued)

FOREIGN PATENT DOCUMENTS

GB   2404920 A   2/2005
JP   2003329667 A   11/2003
(Continued)

OTHER PUBLICATIONS

GB Search Report 1301618.3 dated Jul. 29, 2013.
(Continued)

*Primary Examiner* — Jezia Riley
(74) *Attorney, Agent, or Firm* — Eversheds Sutherland (US) LLP

(57) ABSTRACT

This invention relates to flat solid media for the storage of samples of biological materials and methods of analyzing biomolecules contained within the samples following storage. In particular, the invention relates to the storage and further analysis of biomolecules present in the biological materials, such as proteins, enzymes and nucleic acids. The invention finds particular utility in the dry, room temperature storage of biological materials.

27 Claims, 9 Drawing Sheets

Specification includes a Sequence Listing.

(51) Int. Cl.
  *A01N 1/02* (2006.01)
  *C12N 9/22* (2006.01)
  *C12N 9/96* (2006.01)

(52) U.S. Cl.
  CPC ......... *C12N 9/96* (2013.01); *C12Q 2527/125* (2013.01); *C12Y 301/00* (2013.01)

(58) Field of Classification Search
  USPC .................................................. 435/4, 307.1
  See application file for complete search history.

(56) References Cited

U.S. PATENT DOCUMENTS

| | | | |
|---|---|---|---|
| 5,840,777 A * | 11/1998 | Eagles | A61L 15/28 521/134 |
| 5,939,259 A * | 8/1999 | Harvey | C12N 15/1003 435/269 |
| 6,649,406 B1 | 11/2003 | Williams et al. | |
| 6,696,077 B2 | 2/2004 | Scherr et al. | |
| 8,900,856 B2 | 12/2014 | Muller-Cohn et al. | |
| 2007/0225652 A1 | 9/2007 | Scherr | |

FOREIGN PATENT DOCUMENTS

| | | |
|---|---|---|
| JP | 2009-011215 A | 1/2009 |
| WO | 98/24486 | 6/1998 |
| WO | 01/38559 | 5/2001 |
| WO | 2007/144389 | 12/2007 |
| WO | 2007/144389 A2 | 12/2007 |

OTHER PUBLICATIONS

Yoshioka, et.al., Biomaterials, vol. 24, 2003, pp. 2889-2894.
Lee, et.al. J. Biomed. Mat. Res. vol. 36, 1997, pp. 200-208.
Mei, et.al., Journal of Nutruition, vol. 131,2001 pp. 1631S-1636S.
Ryley, et.al. J. Clin. Pathol. vol. 34, 1981, pp. 906-910.
Lindau-Shepard & Pass, Clinical Chem, vol. 56, 2010, pp. 445-450.
Elvers, et.al. Toyo Roshi Grade 545 Advantec Toyo, Tokyo, J. Inherit Medtab Dis vol. 30, No. 4 2007 p. 609.
Bonino, et.al., Carbohydrate Polymers 85, 2011 pp. 111-119.
Percival, et.al., Int. Would Journal vol. 8, No. 3, 2011, pp. 237-243.
Cloud, et.al. Journal Clinical Microbiology, vol. 40, No. 10, 2002 pp. 3838-3840.
Eibak, et.al., Anal Chem, Vol. 84, 2012, pp. 8783-8789.
Hansen, et.al., Appl Environ Microbiol. vol. 47 No. 4, 1984 pp. 704-709.
Japanese Office Action for JP Application No. 2015-554211 dated Nov. 21, 2017 (6 pages).
European Office Action for EP Application No. 14701765.1 dated Jun. 8, 2018 (6 pages).
Japanese Office Action for JP Application No. 2015-554211 dated Sep. 4, 2018.

* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: note=beta-globin exon I 5'-3'/mol_type=
      "unassigned DNA"

<400> SEQUENCE: 1
ggtgaacgtg gatgaagttg                                              20

<210> SEQ ID NO 2
<211> LENGTH: 18
<212> TYPE: DNA
<213> ORGANISM: Homo sapiens
<220> FEATURE:
<221> NAME/KEY: source
<222> LOCATION: (1)..(18)
<223> OTHER INFORMATION: note=beta-globin-exon III 5'-3'/mol_type=
      "unassigned DNA"

<400> SEQUENCE: 2
agcacacaga ccagcacg                                                18
```

SOLID MEDIUM FOR THE STORAGE OF BIOLOGICAL MATERIAL

CROSS REFERENCES TO RELATED APPLICATIONS

This patent application is a continuation of U.S. application Ser. No. 13/798,483, filed Mar. 13, 2013, which claims priority benefit of Great Britain Application No. 1301618.3 filed Jan. 30, 2013, each of which is incorporated herein by reference in their entireties.

FIELD OF THE INVENTION

This invention relates to flat solid media for the storage of samples of biological materials and methods of analysing biomolecules contained within the samples following storage. In particular, the invention relates to the storage, recovery and further processing of biomolecules such as proteins, enzymes and nucleic acids.

BACKGROUND OF THE INVENTION

The use of solid media or supports such as filter paper for the collection and analysis of biological materials such as human blood dates back to the early 1960s, when Dr. Robert Guthrie used dried blood spot (DBS) specimens to measure the biomolecule phenylalanine in newborns for the detection of phenylketonuria (Mei, J., et al., 2001; *Journal of Nutrition*, 131:16315-1636S). This novel application for collecting blood led to the population screening of newborns for the detection of treatable, inherited metabolic diseases. DBS have now been used for over 40 years to screen for a large range of neonatal metabolic disorders including enzymes, proteins and for inherited disease using nucleic acid analysis.

The gathering of biological materials such as DBS specimens is carried out by spotting whole blood, for example, onto a solid support, such as a membrane, glass fiber or paper, either from venous blood or directly from a finger or heel prick, making this method particularly suitable for the shipment of specimens from peripheral clinics to central laboratories. Furthermore, DBS packed in zip-lock plastic bags with desiccant can be stored and shipped at ambient temperature, thus avoiding the need for i) cold chain storage and ii) fast specialized transportation. DBS collected by applying a drop of blood onto an absorbent material such as Whatman 903 Neonatal STD paper are not subject to the IATA Dangerous Goods Regulations (Addendum II, March 2005).

Commonly, analysis of DBS is carried out for the presence of infectious agents such as for the presence of human immunodeficiency virus (HIV) or other pathogens. Typically serological or nucleic acid tests are carried out for this application.

The combination of DBS and the detection of endogenous protein biomolecules has been described in the scientific literature; for example, the biomarker for cystic fibrosis (CF) is immunoreactive trypsin (IT). The first reported use of endogenous IT from DBS for CF screening was published by Ryley et al., in 1981 (*J. Clin. Pathol.* 34, 906-910). Since then, it has been routinely used as an indicator of CF using DBS from neonates. A number of commercial organisations supply FDA approved immunoassay kits for this application. Many simply use a "paper-in" approach, in which a paper punch containing the DBS is applied directly in to the immunoassay and the analyte of interest is extracted in situ. Recently (Lindau-Shepard & Pass, 2010, *Clinical Chem.* 56, 445-450) demonstrated that IT exists in two different isoforms. These authors reported the development of a suspension (or paper-in) array-based immunoassay for the diagnosis of CF using the two different isoforms of IT. All these protein-based studies were carried out on uncoated Guthrie cards (Whatman 903 paper).

Since the inception of anonymous human immuno-deficiency (HIV) screening, over 1.2 million DBS tests have been carried out for the serological detection of endogenous anti-HIV antibodies in the blood from expectant mothers. These studies have proved that i) concerns about long-term storage of blood and any associated proteins of interest have proved unfounded and ii) the presence of haem in the DBS does not interfere with assay performance.

Additional solid paper supports that are used for collecting, transportation and storing DBS and other bodily fluids for newborn and neonatal screening purposes include
1. Ahlstrom 226
2. Munktell TFN (CE marked)
3. Toyo Roshi grade 545 Advantec Toyo, Tokyo (see Elvers L et al 2007; *J. Inherit Medtab Dis* 30, 4, 609).

Slow desiccation or even a small degree of rehydration under conditions of high relative humidity will allow the growth of biomolecule-destroying microflora. Even in the presence of bacteriostatic agents of the type that do not denature proteins, there will be conditions that permit enzymatic-autolytic breakdown of the biomolecule and some non-enzymatic breakdown of the biomolecule (in enzymatic-autolytic breakdown, dying or damaged tissues, either human cells or parasite cells, activate enzymes that degrade their own components). With nucleic acids, there is also considerable difficulty desorbing very high molecular weight DNA from paper matrices. Surface adsorption effects can cause losses of DNA and this will cause the preferential loss of the least degraded, i.e. the most desired class of DNA molecules. Thus the long-term archiving of biomolecules is a desirable feature of a storage medium.

Molecular and Nucleic Acid Analyses

The polymerase chain reaction (PCR) is a common tool used in molecular biology for amplifying nucleic acids. U.S. Pat. No. 4,683,202 (Mullis, Cetus Corporation) describes a process for amplifying any desired specific nucleic acid sequence contained in a nucleic acid or mixture thereof. Furthermore, U.S. Pat. No. 5,593,824 and U.S. Pat. No. 5,763,157 (Treml) describe biological reagent spheres useful for the PCR reaction. Additionally, this invention describes a convenient approach by means of excipient mixes comprising suitable carbohydrates useful for storage of reagents used in downstream genetic analysis such as PCR. Carbohydrates are preferably Ficoll and melezitose. This technology has been commercialised in a ready to go (RTG) PCR format (GE Healthcare).

Long-term storage, transport and archiving of nucleic acids on filter paper or chemically modified matrices is a well-known technique for preserving genetic material before the DNA or RNA is extracted and isolated in a form for use in genetic analysis such as PCR. Thus, EP 1563091 (Smith et al., Whatman) relates to methods for storing nucleic acids from a sample such as cells or cell lysates. The nucleic acid is isolated and stored for extended periods of time at room temperature and humidity, on a wide variety of filters and other types of solid phase media. The document describes methods for storing nucleic acid-containing samples on a wide range of solid phase matrices in tubes, columns, or multiwell plates.

Cellulose derived solid supports are described by reference to the following prior art.

WO 90/003959 (Burgoyne) describes a solid medium for the storage of DNA, including blood DNA, comprising a solid matrix having a compound or composition which protects against degradation of DNA incorporated into or absorbed on the matrix. The document also discloses methods for storage of DNA using this solid medium, and for recovery of DNA or in situ use of DNA or RNA.

Forensic and Human Identification Applications

DNA profiling (also called DNA testing, DNA typing, or genetic fingerprinting) is a technique employed by forensic scientists to assist in the identification of individuals by their respective DNA profiles. DNA profiles are encrypted sets of numbers that reflect a person's DNA makeup, which can also be used as the person's identifier. DNA profiling should not be confused with full genome sequencing. It is used in, for example, parental testing and criminal investigations.

The method of DNA profiling is based on PCR using short tandem repeats of nucleotide sequences. This method uses highly polymorphic regions that have short repeated sequences of DNA (the most common is 4 bases repeated, but there are other lengths in use, including 3 and 5 bases). Because unrelated people almost certainly have different numbers of repeat units, short tandem repeats (STRs) can be used to discriminate between unrelated individuals. These STR loci (locations on a chromosome) are targeted with sequence-specific primers and amplified using PCR. The DNA fragments that result are then separated and detected using electrophoresis. There are two common methods of separation and detection, capillary electrophoresis (CE) and gel electrophoresis.

Clinical Applications

A number of DNA databases created from babies' blood samples also exists. Blood samples taken in heel-prick tests to screen for serious conditions are being held for years by some hospitals and can be subsequently accessed by the police to identify people involved in crimes. The samples can also be used by coroners and medical researchers for a variety of purposes. Blood spot screening is carried out on babies aged between five and eight days old in order to test for a variety of serious conditions such as cancer, tumour marking and archiving, sickle cell, PKU and cystic fibrosis. Government guidelines advise hospitals to store the samples for at least five years before destroying them.

In Denmark, for example, Danish Newborn Screening Biobank at Statens Serum Institut retains a blood sample from all neonates born after 1981. The purpose is to test for PKU and other diseases. This database is also used for DNA tests to identify deceased and suspected criminals.

With all the applications outlined above, however, there is a great need for new advances for improved inert matrices that are convenient, safe and confer stability to the biomolecules which is to be analysed. For example, while Burgoyne (U.S. Pat. No. 5,756,126) describes a medium for analysis of genetic material, no reference is made to other biomolecules such as proteins, polypeptides and metabolites.

Pathogens and Infectious Agents

Infectious diseases, also known as contagious diseases or transmissible diseases, and including communicable diseases, comprise clinically evident illness (i.e., characteristic medical signs and/or symptoms of disease) resulting from the infection, presence and growth of pathogenic biological agents in an individual host organism. In certain cases, infectious diseases may be asymptomatic for much or their entire course. Infectious pathogens include viruses, bacteria, bacterial spores, fungi, protozoa, and, multicellular parasites. These pathogens are the cause of disease epidemics, in the sense that without the pathogen, no infectious epidemic occurs. Common examples of infectious agents include *Staphylococcus aureus, Pseudomonas aeruginosa, Escherichia coli, Salmonella choleraesuis* and *Candida albicans* and those that cause sexually transmitted disease or septicaemia. Common microorganisms that are routinely isolated from wounds, using clinical swabs, have included *Staphylococcus aureus, Corynebacterium* sp, *Candida albicans* and *Pseudomonas aeruginosa*.

Transmission of pathogen can occur in various ways including physical contact, contaminated food, body fluids, objects, airborne inhalation, or through vector organisms, so safe capture of infectious agent would be of significant value during any diagnostic workflow. Infectious diseases that are especially infective are sometimes called contagious and can be easily transmitted by contact with an ill person or their secretions. Infectious diseases with more specialized routes of infection, such as vector transmission or sexual transmission, are usually regarded as contagious. Thus inactivation of the target pathogen may be useful prior to diagnostic testing. Sample types may include: pathological specimens from human or samples from veterinary medicine e.g. blood, urine, semen, vaginal secretions, faecal samples, CSF, tissue, lung lavage, sputum, nasopharyngeal samples, cell cultures, soil, water supplies, stream or river samples, aerial.

Once dry, samples could be transported and stored in a dark and dry environment. These simple conditions will ensure that the integrity of the biological sample on the solid medium/card is maintained. No specific temperature control is required for either storage or transport, as both are carried out at room temperature.

Alginate

Alginate, a salt of alginic acid, is extracted from marine kelp (seaweed). The calcium, sodium, and ammonium alginates have been used in foam, cloth, and gauze for absorbent surgical dressings. Soluble alginates, such as those of sodium, potassium, or magnesium, form a viscous sol that can be changed into a gel by a chemical reaction with compounds such as calcium sulphate. Salts of alginic acid with monovalent cations (Na-salt, K-salt, NH4-salt) as well as Alginate Ester are all soluble to cold and hot water, and generate viscous aqueous solution with long-flow properties. Alginic acid and calcium alginate are water-insoluble.

Alginic acid is substantially insoluble in water. It forms water-soluble salts with alkali metals, such as sodium, potassium, and, lithium; magnesium; ammonium; and the substituted ammonium cations derived from lower amines such as methyl amine, ethanol amine, diethanol amine, and triethanol amine.

Alginate absorbs water quickly, which makes it useful as an additive in dehydrated products, and is well known as an additive in the manufacture of paper and textiles to facilitate printing with ink and/or dye products. Accordingly, paper producers are familiar with usage of alginate components, such as sodium alginate, during manufacturing and processing. Sodium alginate can make paper glossy and smooth and it raises the paper's absorption to printing ink and increases its pliability and toughness.

Alginate dressings are natural wound dressings derived from different types of algae and seaweeds. These types of dressings are best used on wounds that have a large amount of exudate and may also be applied onto dry wounds after normal saline is first applied to the site of application.

U.S. Pat. No. 5,820,998 (Schweitzer Maudit Int Inc.) describes a process of making a coated paper for wrapping papers used in smoking articles comprising the steps: 1) providing a paper layer composed of a blend of pulp fibers and particulate material containing polyvalent metal cations, 2) applying a acidified alginate solution of a material selected from salts and derivatives of alginic acid to cover at least a portion of the paper, 3) reacting the salts and/or derivatives of alginic acid with polyvalent metal cations in the paper to form a polymer coating, and 4) drying the paper and polymer coating. The permeability of the coated paper is generally at least about 75 percent less than the permeability of an identical uncoated portion of the paper.

Bonino et al. (2011 Carbohydrate Polymers 85, 111-119) describes the electrospinning of alginate-based nano-fibres.

U.S. Pat. No. 5,482,932 (Courtaulds Fibres (Holdings) Ltd) describes alginate gels which have the form of a fibrous paste and which particularly have an alginate content (expressed as alginic acid) in the range 2 to 11 percent by weight. The gels may be prepared by treating a water-insoluble or water-swellable alginate fibre, for example calcium alginate fibre, with an aqueous solution of a solubilizing salt, for example sodium chloride. The new gels are easier to handle than known alginate gels and are useful in wound dressing applications.

Calcium alginate is a water-insoluble, gelatinous, cream coloured substance that can be created through the addition of aqueous calcium chloride to aqueous sodium alginate. Calcium alginate can be used for entrapment of enzymes and forming artificial seeds in plant tissue culture. It is also incorporated into wound dressings as a homeostatic agent.

Sodium alginate is a gum, extracted from the cell walls of brown algae. As a flavourless gum, it is used by the foods industry to increase viscosity and as an emulsifier. It is also used in indigestion tablets and the preparation of dental impressions. Other applications include use in reactive dye printing, as a thickener for reactive dyestuffs, in textile screen-printing and in carpet jet-printing.

Potassium alginate is the potassium salt of alginic acid. It is an extract of seaweed and is widely used in foods as a stabilizer, thickener, and emulsifier. Its use as a pharmaceutical excipient is currently limited to experimental hydrogel systems. The viscosity, adhesiveness, elasticity, stiffness, and cohesiveness of potassium alginate hydrogels have been determined and compared with values from a range of other hydrogel-forming materials.

Silver alginate is known to have antimicrobial activity. For example, some alginate wound dressings contain a silver alginate, which provides antimicrobial protection and may be considered for an infected wound.

U.S. Pat. No. 6,696,077 (Scherr) relates to the preparation of cellulosic foam products prepared from silver alginate and derivatives thereof and process for preparing them.

U.S. Pat. No. 7,344,726 (Chitoproducts Ltd) discloses a process for the preparation of an article having a contact biocidal property comprising a polymer solution which contains atomic/metallic silver in suspension or complexed with the polymer.

Percival et al (2011 Int. Wound J. 8 (3) 237-243) describes the antimicrobial efficacy of a silver alginate dressing against a broad spectrum of clinically relevant wound isolates.

Cloud et al. (2002 J Clin Microbiol. 40(10): 3838-3840) compared the performance of various swabs and transport media routinely used to collect specimens submitted for *Bordetella* culture and PCR. The authors reported that calcium-alginate swabs inhibited the PCR and recommended that calcium-alginate swabs should not be used for PCR detection of *B. pertussis*.

Eibak et al. (2012 Anal. Chem. 84, 8783-8789) demonstrated the storage and recovery of model substances (citalopram, loperamide, methodone and sertraline) from DBS spotted sodium alginate foams using electromembrane extraction and liquid chromatography-mass spectrometry analysis. The authors reported that lower recoveries were obtained with the commercial cards (i.e. Whatman FTA DMPK and Agilent Bond Elut DMS) for most of the model substances compared to the recoveries with the alginate foam.

The present invention addresses the problems associated with the room temperature, dry storage and subsequent analysis of biomolecules present in samples of biological materials and provides an alternative solution to those known or suggested by the prior art. Moreover, the invention further provides a means for inactivating microbial pathogens which may be present in the biological material.

SUMMARY OF THE INVENTION

According to a first aspect of the present invention, there is provided a flat solid medium for storing at least one sample of a biological material containing a biomolecule, the solid medium comprising a solid matrix having sorbed thereto or incorporated therein a composition comprising an alginate.

It will be understood that the composition of alginate, present for example as fibres, may be woven throughout the solid matrix.

The invention is particularly useful in genotyping, diagnostics and, predominantly, forensics applications, with amplification of low copy number genes or low expression mRNA; short tandem repeats (STRs), alleles, loci, or other genetic materials, derived from crude biological samples.

In one aspect, the solid medium additionally comprises a protein denaturing reagent. The protein denaturing reagent can lyse cell membranes and thus provide antimicrobial activity and/or will release biomolecules and cellular components onto the solid medium, thereby preventing degradation of the biological material by enzymatic activity. The protein denaturing reagent may be an ionic or anionic detergent such as sodium dodecyl sulphate (SDS) or sodium lauryl sarcosinate.

In one preferred embodiment, the ionic detergent of the invention causes inactivation of a microorganism which has protein or lipid in its outer membranes or capsids, for example, fungi, bacteria or viruses. This includes microorganisms which may be pathogenic to humans or which may cause degradation of the biomolecule.

In another aspect, the solid medium additionally comprises a free radical trap. Examples of free radical traps include uric acid or a urate salt. Typically, free radicals are believed to be generated by spontaneous oxidation of the groups which are present, for example, in denatured serum protein of blood. Free radicals may also be generated by radiation such as UV light, x-rays and high-energy particles.

In a further aspect, the solid medium additionally comprises a chelating agent. As used herein, a chelating agent is any compound capable of complexing multivalent ions including Group II and Group III multivalent metal ions and transition metal ions (eg., Cu, Fe, Zn, Mn, etc). According to the invention, a preferred chelating agent is a strong chelating agent such as to ethylene diamine tetraacetic acid (EDTA). Chelating agents such as a citrate or oxalate are also suitable for the invention.

It is believed that one function of the chelating agent of the invention is to bind multivalent ions which if present with the stored biomolecule may partake in causing damage to the biomolecule, particularly nucleic acid. Ions which may be chelated by the chelating agent include multivalent active metal ions, for example, magnesium and calcium, and transition metal ions, for example, iron. Both calcium and magnesium are known to promote nucleic acid degradation by acting as co-factors for enzymes which may destroy nucleic acid (e.g., most known nucleases). In addition, transition metal ions, such as iron, may readily undergo oxidation and reduction and damage nucleic acids by the production of free radicals or by direct oxidation.

In one aspect, the solid medium additionally comprises a chaotrophic salt. Guanidine salt is an example of a chaotrophic salt.

In a further aspect, the alginate is selected from the group consisting of calcium alginate, sodium alginate, potassium alginate, ammonium alginate, magnesium alginate, lithium alginate and silver alginate.

In one aspect, the alginate has antimicrobial activity.

In a preferred aspect, the alginate is silver alginate.

Candidates for co-coating purposes which facilitate pathogen inactivation or biomolecules storage include mild detergents (e.g. Triton, SDS), chelating agents (e.g. EDTA) and uric acid or a urate salt in order to facilitate stability and to act as a free radical trap.

Paper or inert matrix could be modified directly (or simply coated) with chemical groups that will support the elution (if needed) of a specific biomolecule. This selective elution could be based upon for example; ion exchange mechanisms (alginate as a bio-carrier will mainly rely on charged chemical moieties).

Enzymes that hydrolyse alginates are known, which will prove useful to liberate nucleic acid, protein or other biomolecules captured on the coated support. Alginase enzyme production from cultured Bacillus circulans is described in Hansen et al. (1984) (Appl Environ Microbiol. 47(4): 704-709).

Paper or other suitable matrices could be co-coated with alginate and/or modified with a number of different chemicals, all of which will alter the surface properties so that it becomes resistant to irreversible biomolecule absorption, thereby facilitating that elution of the biomolecule of interest.

Additional candidates for co-coating include—
a) Self-assembled monolayer of alkanethiols.
b) Polyethylene glycol which has been used as a coating for biomedical devices.
c) Other surface-grafted polymers that resist the adsorption of protein include polyvinyl alcohol (PVA), polyethyloxazoline (PEOX), poly(vinylpyrrolidone), (PVP) and poly(ethyleimine) (PEI).
d) An alternative is the preparation of papers that possess a hydrophobic surface.
e) A further refinement include co-coating one of the surface-grafted polymers described above with a protein (e.g. horse IgG, albumin) to further enhance biomolecule elution.

In another aspect, the solid matrix is selected from the group consisting of a cellulose matrix, a nitrocellulose matrix, a carboxymethylcellulose matrix, a polyester matrix, a polyamide matrix, a polytetrafluoroethylene matrix, a fibreglass matrix and a porous ceramic matrix. Other solid matrices suitable for this purpose include, but are not limited to, hydrophilic polymers including synthetic hydrophilic polymers such as polyester and carbohydrate polymers).

In a preferred aspect, the solid matrix is a cellulose matrix.

In a particularly preferred aspect, the solid matrix is a cellulose matrix and the alginate is silver alginate.

In one aspect, the sample of biological material is selected from the group consisting of eukarytic cell, prokaryotic cell and prion cell. In particular, the sample of biological material is selected from the group consisting of blood, plasma, saliva, urine and buccal cells.

In another aspect, the sample of biological material contains a biomolecule selected from the group consisting of nucleic acid, protein, biopharmaceutical and polysaccharide.

In a further aspect, the solid medium additionally comprises a sample of a biological material stored thereon.

In one aspect, the solid medium additionally comprises a sample of an analytical process. For example, the sample is a liquid chromatography analysis, or an HPLC analysis.

According to a second aspect of the present invention, there is provided a method for storing a sample of a biological material containing a biomolecule on a flat solid medium comprising the steps of
a. applying a sample of a biological material containing a biomolecule to a flat solid medium comprising alginate or comprising a solid matrix having sorbed thereto or incorporated therein a composition comprising an alginate; and
b. storing said sample of biological material on said flat solid medium.

It will be understood that the flat solid medium of the second aspect may consist totally of alginate or be composed of alginate fibres. In another embodiment, the composition of alginate, present for example as fibres, may be woven throughout the solid matrix.

In one aspect, the sample is stored on the dry solid medium without refrigeration.

In another aspect, the sample is stored on the dry solid medium at a temperature in the range of 4° C. to 50° C. Typically aqueous biological samples are stored at low temperatures in freezers or fridges to prevent cellular degradation and microbial growth. The method of the invention avoids the problems associated with low temperature storage and transport, in terms of the cost of buying and running fridges and freezers, together with the space requirements of such equipment. Transport of the samples is also facilitated since the dry solid media can be sent through the post without the need for any cooling.

In one aspect, the sample is stored on the solid medium for a period of at least 1 day. Indeed the sample can be stored on the dry solid medium for a period selected from the group consisting of at least 1 week, at least 1 month, at least 6 months, at least 9 months, at least 1 year, at least 2 years, at least 5 years, at least 10 years, at least 15 years and at least 20 years.

According to a third aspect of the present invention, there is provided a method of analysing a sample of a biological material containing a biomolecule stored on a flat solid medium, the flat solid medium comprising alginate or comprising a solid matrix having sorbed thereto or incorporated therein a composition comprising an alginate, comprising the step of analysing the biological material for the presence and/or level of a biomolecule.

It will be understood that the flat solid medium of the third aspect may consist totally of alginate or be composed of alginate fibres. In another embodiment, the composition of alginate, present for example as fibres, may be woven throughout the solid matrix.

Methods for analysing the biomolecule present in the biological material include for example, but are not limited to, nucleic acid amplification by the polymerase chain reaction (PCR), short tandem repeat for human identification purposes and DNA profiling, isothermal amplification, additionally serological testing using antibodies, lateral flow, antibody based tests such as enzyme-linked immunosorbent assay (ELISA), Western blotting, fluorescence energy resonance transfer, mass spectrometry, GC/MS and tandem mass spectrometry.

The biomolecule is selected from the group consisting of nucleic acid, protein, biopharmaceutical and polysaccharide.

In one aspect, the step of analysing the biological material for the presence and/or level of a biomolecule is carried out directly on the solid medium or a portion thereof. For example, the portion may be a disc which can be cut or punched from the sold support into a test tube or well of a multi-well plate and then assayed for the presence and/or level of a biomolecule. This process may be carried out manually or automatically using standard robotic laboratory equipment.

In another aspect, the method additionally comprises the step of eluting the biological material from the solid medium prior to analysing the biological material for the presence and/or level of the biomolecule. It will be understood that this process may be carried out manually or automatically using standard robotic laboratory equipment.

In a further aspect, the solid medium additionally comprises a protein denaturing reagent. The protein denaturing reagent can be, for example, a detergent such as a sodium dodecyl sulphate.

In yet another aspect, the solid medium additionally comprises a free radical trap. For example, the dry solid medium may comprise uric acid or a urate salt.

In one aspect, the solid medium additionally comprises a chelating agent. EDTA is an example of a suitable chelating agent.

In another aspect, the solid medium additionally comprises a chaotrophic salt. An example of a suitable chaotrophic salt is a guanidine salt.

In a further aspect, the alginate is selected from the group consisting of calcium alginate, sodium alginate, potassium alginate, ammonium alginate, magnesium alginate, lithium alginate and silver alginate.

In one aspect, the alginate has antimicrobial activity.

In a preferred aspect, the alginate is silver alginate.

In a further aspect, the solid matrix is selected from the group consisting of a cellulose matrix, a nitrocellulose matrix, a carboxymethylcellulose matrix, a polyester matrix, a polyamide matrix, a polytetrafluoroethylene matrix, a fibreglass matrix and a porous ceramic matrix.

In one aspect, the solid matrix is a cellulose matrix.

In a preferred aspect, the solid matrix is a cellulose matrix and the alginate is silver alginate.

In another aspect, the sample of biological material is selected from the group consisting of the group consisting of eukarytic cell, prokaryotic cell and prion cell. In particular, the biological material is selected from the group consisting of blood, saliva, plasma, urine and buccal cells.

In a further aspect, the sample of biological material contains a biomolecule selected from the group consisting of nucleic acid, protein, biopharmaceutical, polysaccharide and cellular component.

According to a fourth aspect of the present invention, there is provided a kit of parts, comprising a flat solid medium as hereinbefore described and instructions for use.

According to a fifth aspect of the present invention, there is provided a use of a flat solid medium as hereinbefore described for collecting or storing or analysing a sample of a biological material.

BRIEF DESCRIPTION OF THE FIGURES

FIG. 3A shows the profile obtained from the alginate coated matrix; FIG. 3B shows the profile from the FTA paper; and FIG. 3C shows the profile from the 903 paper.

FIG. 4A shows the detection of DNase (0.125-0.5 U) which had been added to alginate, 903 and FTA Matrices. FIG. 4B shows the detection of DNase activity following the addition of native DNase (0.5 U) to matrices having Human Embryonic Stem ($10^6$) Cells Applied to the alginate, 903 and FTA matrices. FIG. 4C shows the detection of RNase activity following the addition of native RNase (10 μU) to matrices having Human Embryonic Stem Cells ($10^6$) Cells applied to the alginate, 903 and FTA matrices.

FIG. 5 shows the results from RT PCR of β-Globin Gene Fragment from human embryonic stem cells. The results are shown as agarose gel (2%) electrophoresis of the RT-amplified product in which:

Figure 1:
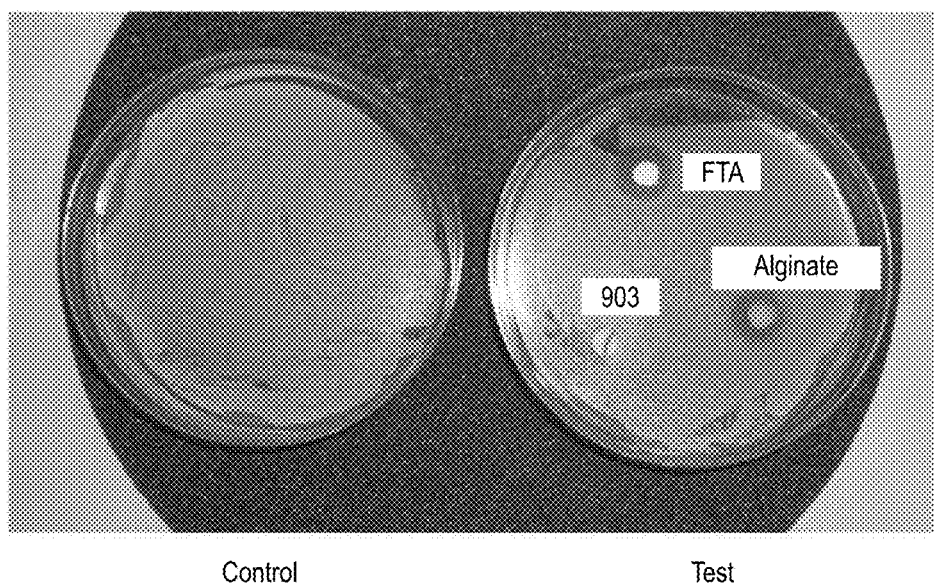
FIG. 1 shows the results of a bacterial growth inhibition test. Alginate and FTA discs exhibited zones of inhibition whereas 903 (uncoated paper) did not. Control dishes exhibited typical bacterial lawns.

Lane 1: No Template control.
Lane 2: RNA template isolated from the alginate matrix using RNA spin; amplified β-globin gene fragment.
Lane 3: Negative control—un-extracted whole blood sample.
Lane 4: Negative control—un-extracted whole blood sample.
Lane 5: Negative control—un-extracted whole blood sample.
Lane 6. Internal Control Sample.
Lane 7: No Template Control.

DETAILED DESCRIPTION OF THE INVENTION

Definitions

To more clearly and concisely describe and point out the subject matter of the claimed invention, the following definitions are provided for specific terms, which are used in the following description and the appended claims. Throughout the specification, exemplification of specific terms should be considered as non-limiting examples.

The term "flat" as used herein will mean a generally smooth, even sheet- or card-like structure which is horizontally level.

As used herein, the term "biological material" shall include any material or sample originating from, derived from or obtained from a biological source. Examples will include samples of human or animal origin, such as saliva, blood, plasma, urine and buccal cells. Other examples include samples from cell cultures of animal, plant, bacterial, fungal or viral origin. Yet other examples include samples containing pathogens, such as saliva, blood, plasma, urine and buccal cells. Further examples include cellular components, e.g. organelles.

The term "biomolecule" as used herein shall mean any "biomolecule" or "synthetically-derived biomolecule" as defined below:

i) A biomolecule is any organic molecule that is produced by a living organism, including large polymeric molecules such as proteins, polysaccharides, and nucleic acids as well as small low molecular weight molecules such as primary metabolites, secondary metabolites, and natural products.

ii) A synthetically-derived biomolecule is a "biomolecule" as defined in i) above that is generated using recombinant DNA technologies or chemically synthesised by other non-living in-vitro methods.

iii) The term "nucleic acid" is used herein synonymously with the term "nucleotides" and includes DNA, such as plasmid DNA and genomic DNA; RNA, such as mRNA, tRNA, sRNA and RNAi; and protein nucleic acid, PNA.

iv) A "biopharmaceutical" is a biomolecule as defined by any of i) to iii) above which is designed or produced as a drug or drug candidate.

As used herein, the term "sorb" means that the composition of the invention is absorbed, adsorbed, coated or otherwise incorporated into or onto a solid matrix in such a way as not to be readily removed from the matrix unless subjected to conditions which are intentionally or inadvertently performed to remove the sorbed composition from the solid matrix.

"Alginate" as used herein is the term usually used for the salts of alginic acid, but it can also refer to all the derivatives of alginic acid and alginic acid itself.

Herein, the term "room temperature" shall mean a temperature between 4 and 50 degrees Celcius.

Materials

The Alginate Matrix (Urgosorb, silver alginate wound dressing, Lot 36943, was obtained from Urgo Medical (Urgo Limited, Sullington Road, Shepshed, Loughborough, UK, LE12 9JG), 903 (W101, lot 6891711) and Indicating FTA cards (WB650060, Lot FTA6903311) were obtained from GE Healthcare (GE Healthcare Life Sciences, Amersham Place, Little Chalfont, Buckinghamshire, HP7 9NA UK).

Alternative Methods for Preparing Alginate Matrices

Other methods, which are well known in the art, can be used to prepare solid supports according to the present invention.

For example, to 10 ml of ethyl alcohol is added with stirring, 2 g of sodium alginate and 1 g of sodium hypochlorite. 10 ml of deionised water is added and the resultant mixture incubated at room temperature for 24 hours. A solid support is immersed into the liquid containing sodium alginate and quickly immersed in a solution of aqueous 5% (w/v) calcium chloride which is used to convert the sodium alginate to calcium alginate. The solid support is removed, excess liquid squeezed off and the solid support washed with distilled water. After washing, the solid support is dried by passing over heated rollers. The dried coated material is mechanically softened (micrexed) to produce a plaint material. The calcium alginate forms a hydrogel. The amount of alginate added to the solid support can vary from between 2-100% (w/v).

Alternatively solution sodium alginate/calcium alginate may be added to the solid support directly in the presence of glycerine as a wetting agent and ethyl alcohol to prevent a gel formation. The coated material is dried as above.

To prepare a matrix comprising silver alginate, calcium alginate is prepared using a mixture containing for example silver nitrate, silver proteinate, silver sulfadiazine, or silver acetate, and this mixture is added to the solid support as describe above.

Zone of Inhibition Testing

Disk diffusion antibiotic sensitivity testing is a test which uses antimicrobial-impregnated discs to test whether particular bacteria are susceptible to a specific agent. Known quantities of bacteria are grown on agar plates in the presence of discs containing relevant antimicrobial agent. If the bacteria are susceptible to a particular antimicrobial, an area of clearing surrounds the disc where bacteria are not capable of growing (called a zone of inhibition). This along with the rate of diffusion of the antimicrobial agent is used to estimate the bacteria's sensitivity to the particular antimicrobial agent. In general, larger zones correlate with smaller minimum inhibitory concentration (MIC) of that bacterium.

*Staphylococcus aureus* (ATCC 25923, lot 57941605) were cultured in tryptone soy agar in sterile petri dishes overnight at 37° C. 6 mm discs of alginate coated inert matrix (FTA GE Healthcare) and 903 (GE Healthcare) were applied to the agar surface of the cultures and the cultures again incubated overnight at 35° C. Each bacterial lawn was examined for growth inhibition (zone of inhibition) around each disc. Control cultures consisted of bacterial lawn without the addition of 6 mm disc.

The results from the Zone of Inhibition experiments are shown in FIG. 1. Alginate and FTA discs exhibited zones of inhibition, 903 (uncoated paper) did show any inhibition of bacterial growth. Control dishes exhibited typical bacterial lawns.

This experiment shows the inhibitory nature of the alginate coated matrix to bacterial growth.

Inhibition of Pathogen Replication

Antimicrobial testing was also carried out using the following procedure. *Staphylococcus aureus* (ATCC 25923, lot 57941605) was cultured in Tryptone Soy Broth overnight at 35° C. without shaking. The following day, 100 µl of the neat culture was added to Butterfields Buffer containing 6 mm punches of alginate coated matrix, or 903 paper. The neat cultures were mixed to disrupt the matrices. A dilution series of organism was constructed from $10^{-4}$-$10^{-7}$ cfu in Butterfields Buffer and each sample was allowed to incubate at ambient temperature for 10 minutes. 0.5 ml volumes of each sample were then plated on to Tryptone Soy Agar and the plates were allowed to dry for 10 minutes at ambient temperature. The plates were inverted and cultured overnight at 35° C. Colony counts were carried out the following day and results from alginate matrix were compared with control plates (uncoated 903 paper).

Figure 2:
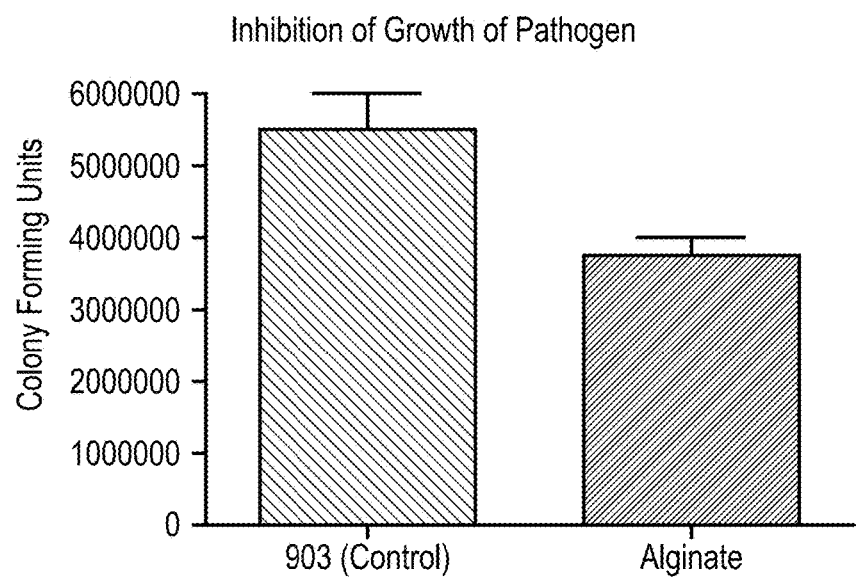
FIG. 2 shows the results of an inhibition of pathogen replication test. Alginate exhibited inhibition of bacterial (*Staphylococcus aureus*) replication while untreated (903 paper) solid media did not.

The results from the pathogen Inactivation experiments are shown in FIG. 2. Alginate exhibited inhibition of pathogen growth, 903 (uncoated paper) did not show any inhibition of bacterial replication. Control dishes exhibited typical bacterial lawns.

This experiment shows the inhibitory nature of the alginate coated matrix to bacterial growth.

Short Tandem Repeat (STR) Profiling of Amplified DNA Sequences

This experiment was carried out to amplify DNA directly for the alginate matrix and to compare results with established matrices such as FTA and 903 (Controls). DNA profiling is described here and is based on PCR which uses short tandem repeats (STR), which are short repeating sequences of base pairs of DNA. This method uses highly polymorphic regions that have short repeated sequences of DNA (the most common is 4 bases repeated. Because unrelated people almost certainly have different numbers of repeat units, STRs can be used to discriminate between unrelated individuals. These STR loci (locations on a chromosome) are targeted with sequence-specific primers and amplified using PCR. The DNA fragments that result are then separated and detected using capillary electrophoresis. Thus, STR loci consist of short, repetitive sequence elements 3-7 base pairs in length. These repeats are well distributed throughout the human genome and are a rich source of highly polymorphic markers, which may be detected using PCR. Alleles of STR loci are differentiated by the number of copies of the repeat sequence contained within the amplified region and are distinguished from one another using fluorescence detection following electrophoretic separation.

Direct amplification of DNA from storage card punches was followed. Direct STR profiling was carried out on duplicate punches using a PowerPlex 21 System (Product code DC8902, Promega, Southampton, UK) over 28 amplification cycles. The PowerPlex 21 System allowed co-amplification and four-colour fluorescent detection of 21 loci (20 STR loci and Amelogenin), including D1S1656, D2S1338, D3S1358, D5S818, D6S1043, D7S820, D8S1179, D12S391, D13S317, D16S539, D18S51, D19S433, D21S11, Amelogenin, CSF1PO, FGA, Penta D, Penta E, TH01, TPOX and vWA. The PowerPlex 21 System provide all materials necessary to amplify STR regions of human genomic DNA, including a hot-start thermostable DNA polymerase, master mix and primers and this kit was used to amplify DNA directly from 1.2 mm punches from $10^6$ human embryonic stem cells (GE Healthcare; cell line ref: WCB307 GEHC 28) applied to alginate coated matrix, FTA and 903 papers. The procedure was followed exactly as outlined in the instruction booklet (PowerPlex 21 System, Promega, Southampton, UK).

Thermal Cycling conditions over 28 cycles were as follows:
96° C. for 1 minute, then:
94° C. for 10 seconds
59° C. for 1 minute
72° C. for 30 seconds
for 28 cycles, then:
60° C. for 20 minutes
4° C. hold The resulting PCR products were analysed on an ABI™ 3130×1 Genetic Analyzer capillary electrophoresis system with GENEMAPPER™ v3.2 software (Life Technologies, Paisley, UK). The STR profiles generated from punches were taken and sample results were compared.

Figure 3A:
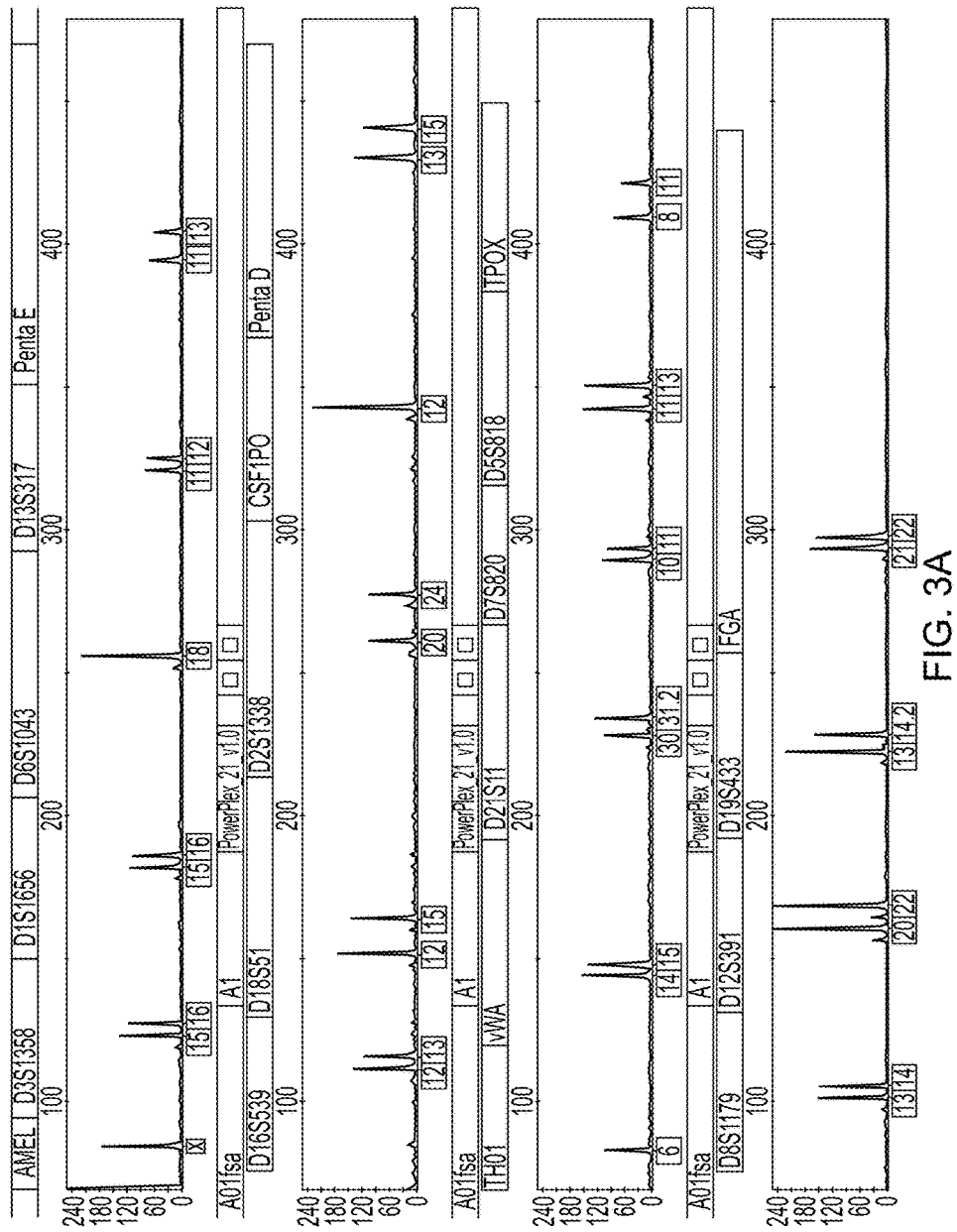
FIGS. 3A, 3B and 3C show the data from the STR/DNA profiling experiments.
Figure 3B:
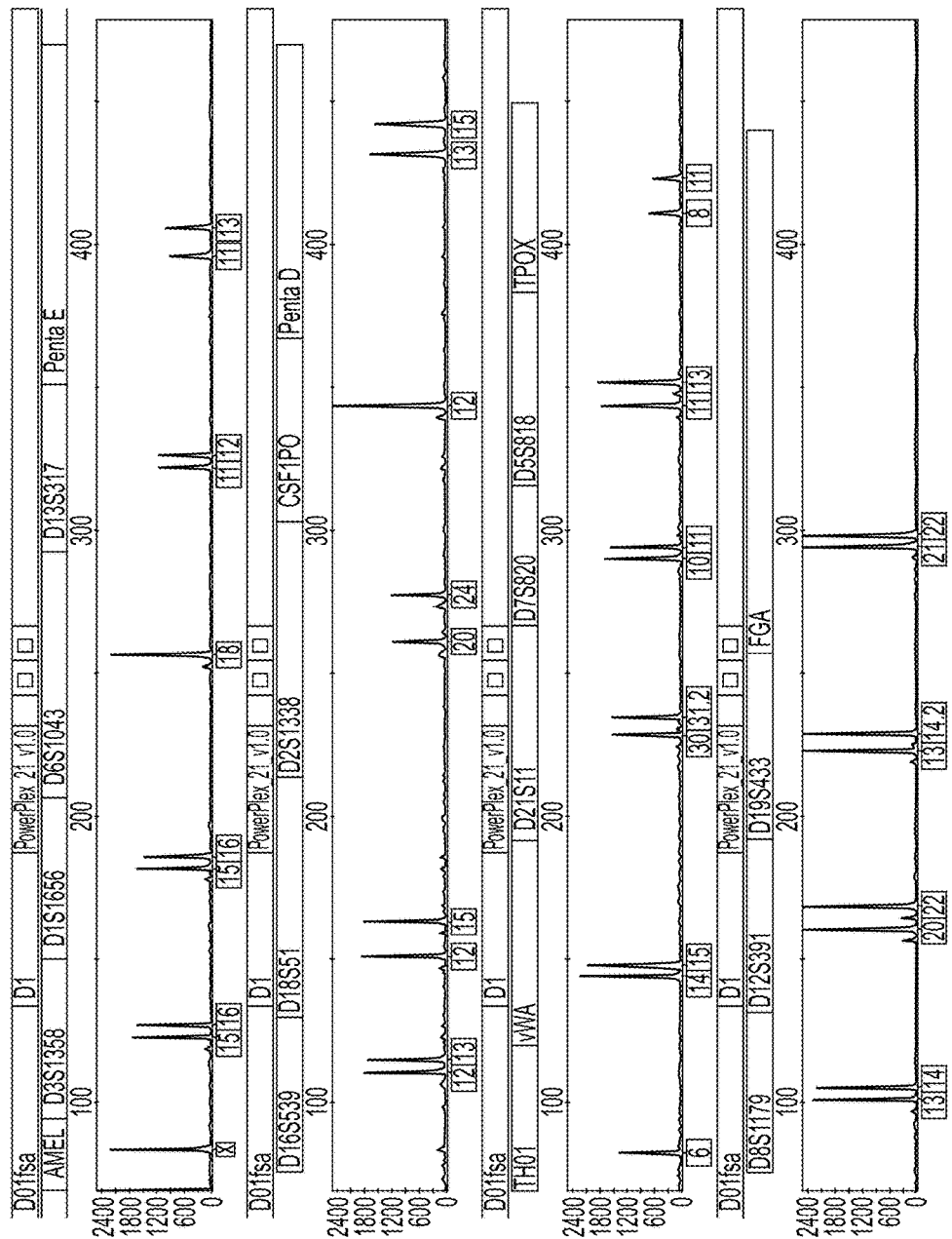
Figure 3C:
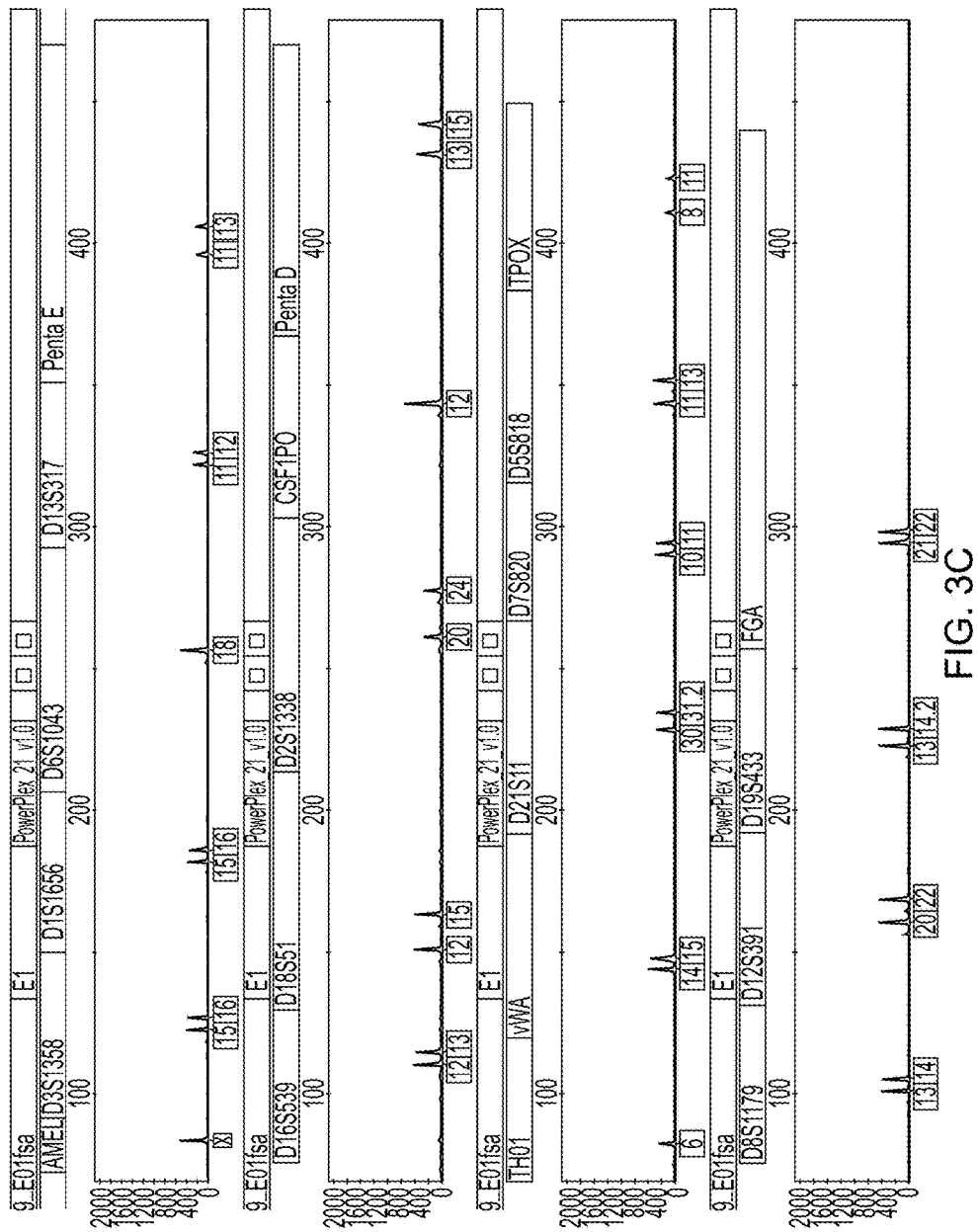

The results of DNA amplification and DNA profiling from the alginate coated matrix, FTA and 903 papers are shown in FIG. 3. Full DNA profiles were obtained from the alginate coated matrix (FIG. 3A), FTA paper (FIG. 3B) and 903 paper (FIG. 3C). The results from the alginate coated matrix (FIG. 3A) indicated that DNA may be stored and amplified from this matrix.

Protein and Enzyme Detection

Protein and enzyme testing was carried out with fully configured DNase and RNase Contamination Kits (DNase & RNase Alert QC Systems, catalogue codes AM1970 & AM1966, Life Technologies) according to the manufacturer's instructions.

In a first series of experiments, 0.125-0.5 U of DNase was applied to alginate coated matrix FTA and 903 paper in 10 µl volumes. DNAse and RNase activity was measured as outlined below.

In a second series of experiments, 1.2 mm punches were taken from $10^6$ human embryonic stem cells (GE Healthcare; cell line ref: WCB307 GEHC 28) which had been applied to alginate coated matrix, FTA and 903 papers in 10 µl volumes as above. DNAse and RNase activity was measured as outlined below.

In a third series of experiments, 1.2 mm punches were taken from $10^6$ human embryonic stem cells (GE Healthcare; cell line ref: WCB307 GEHC 28) containing either 0.5 U of DNase or 10 µU of RNase added to these cells which had been applied to alginate coated matrix, FTA and 903 papers in 10 µl volumes.

Figure 4A:
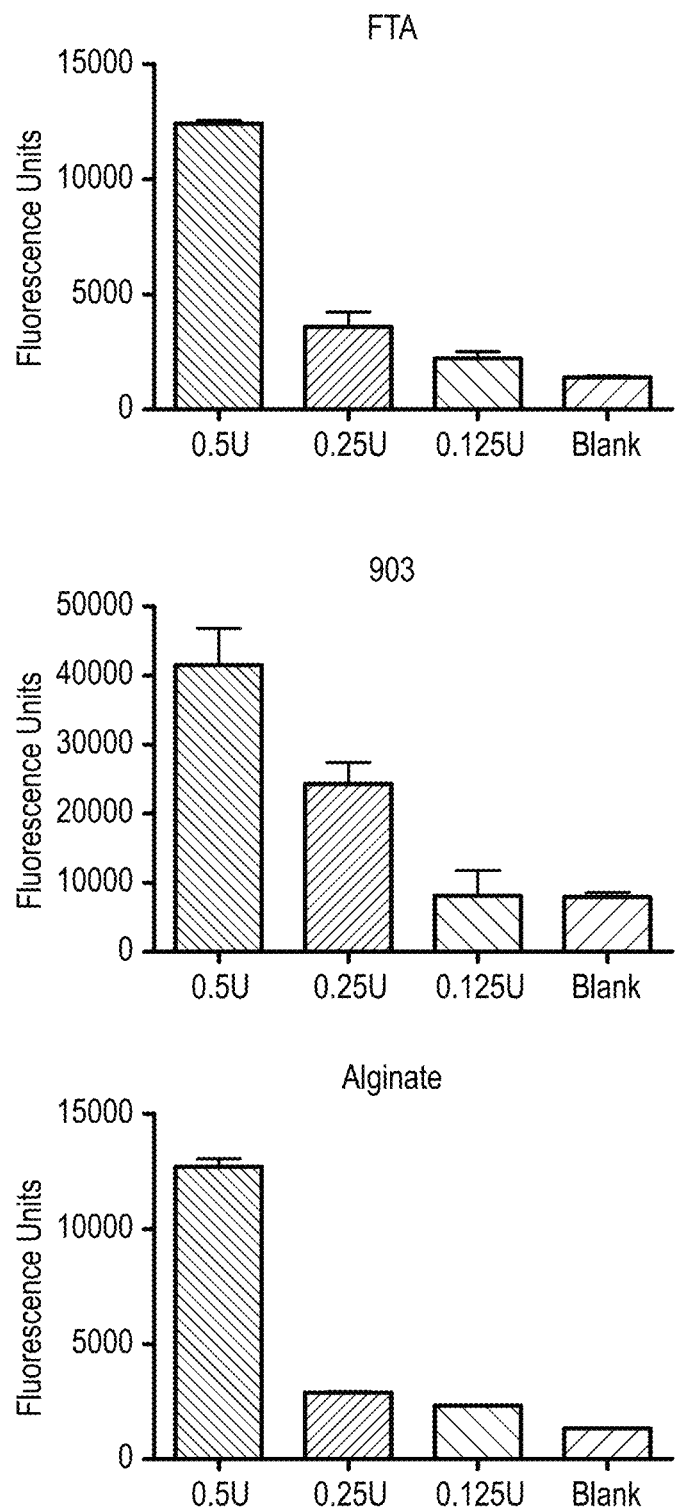
FIGS. 4A, 4B and 4C show the results from experiments to detect protein and enzyme Detection using DNase and RNase as Target Molecules.

Detection of DNase activity was carried out as follows using a cleavable fluorescent-labelled DNase substrate. Each punch was ejected into separate wells of 96-well plates. Lyophilized DNase Alert Substrate was dissolved in TE buffer (1 ml) and dispensed (10 µl) into the test wells of the 96-well plate. 10× DNase Alert Buffer (10 µl) and nuclease-free water (80 µl) was added and the test solution (100 µl) incubated for 60 minutes at 37° C. The DNase Alert QC System Substrate is a modified DNA oligonucleotide that emits a pink fluorescence when cleaved by DNase. For this assay, fluorescence was measured on a Tecan Ultra (excitation/emission 535/595 nm using medium gain). Solutions containing DNase activity produced a pink fluorescence, whereas solutions without DNase activity did not fluoresce. Thus, higher levels of DNase corresponded to an increase in the amount of light output. Negative controls consisted of nuclease-free water (80 µl) in place of sample. FIG. 4A shows that DNAase activity can be detected and quantified in a rate dependent manner using the alginate, 903 or FTA papers.

Figure 4B:
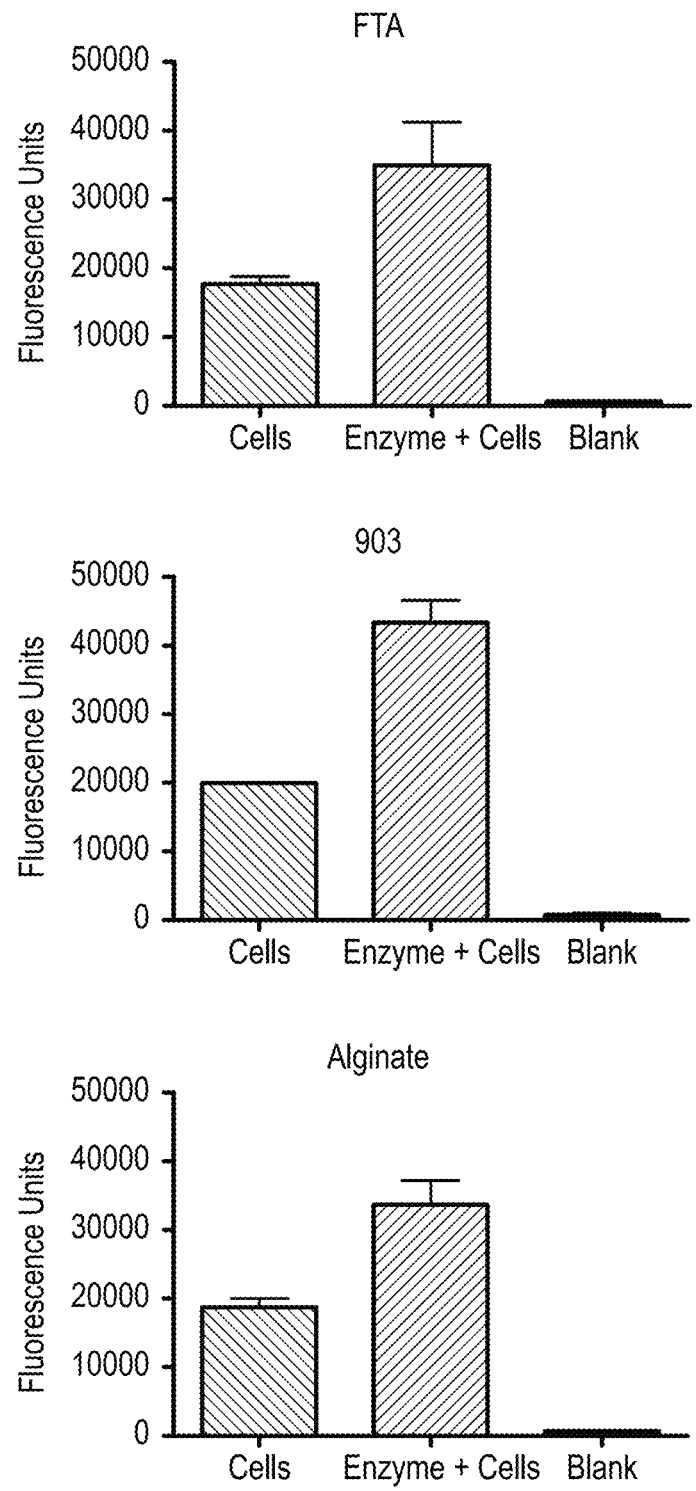
Figure 4C:
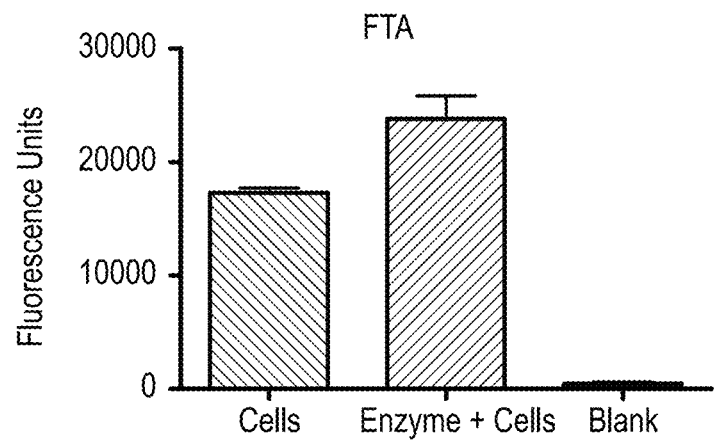
Figure 4C:
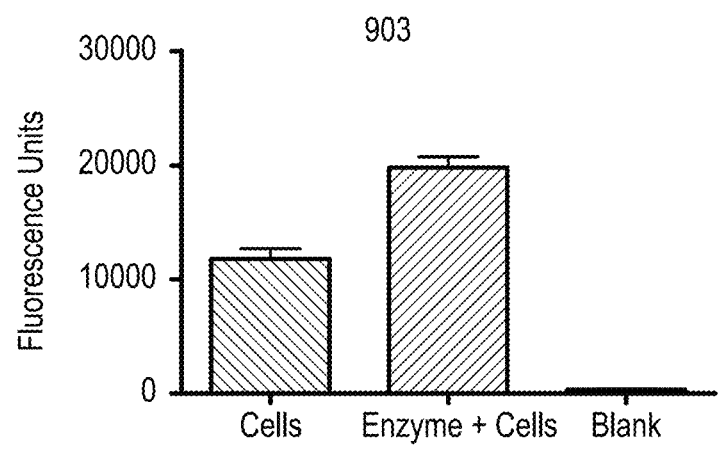
Figure 4C:
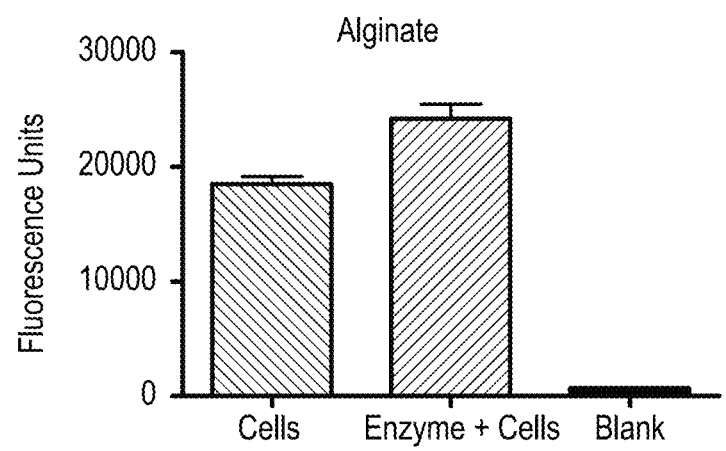

Detection of RNase was carried out as follows using a cleavable fluorescent-labelled RNase substrate. Each punch was ejected into separate wells of 96-well plates. Lyophilized RNase Alert Substrate was dissolved in TE buffer (1 ml) and dispensed (10 µl) into the test wells of the 96-well plate. 10× RNase Alert Buffer (10 µl) and nuclease-free water (80 µl) was added and the test solution (100 µl) incubated for 60 minutes at 37° C. The RNase Alert QC System Substrate is a modified RNA oligonucleotide that emits a green fluorescence when cleaved by RNase. For this assay, fluorescence was measured on a Tecan Ultra (excitation/emission 485/535 nm using medium gain). Solutions containing RNase produced a green fluorescence, whereas solutions without RNase activity did not fluoresce. Thus, higher levels of RNase corresponded to an increase in the amount of light output. Negative controls consisted of nuclease-free water (80 µl) in place of sample. FIG. 4B shows that RNAase activity can be detected and quantifie in a rate dependent manner using the alginate, 903 or FTA papers.

Reverse transcription (RT) PCR of Total RNA

Reverse transcriptase (RT) is an enzyme used to generate complementary DNA (cDNA) from an RNA template, a process termed reverse transcription. Reverse transcriptase creates single-stranded DNA from an RNA template. Reverse transcription polymerase chain reaction (RT-PCR) is one of many variants of PCR. This technique is commonly used in molecular biology to detect RNA expression levels. RT-PCR is used to qualitatively detect gene expression through creation of complementary DNA (cDNA) transcripts from RNA. RT-PCR is used to qualitatively detect gene expression through creation of cDNA transcripts from RNA. The technique using of end-point RT-PCR requiring the detection of gene expression levels by the use of a fluorescent dye incorporated into an agarose gel is reported here.

$10^7$ human embryonic stem cells (GE Healthcare; cell line ref: WCB307 GEHC 28) were applied to alginate coated matrix. Total RNA was extracted from this matrix using an illustra RNAspin mini RNA isolation kit (GE Healthcare, Product Code 25-0500-70). Total RNA was prepared exactly as described in the instruction booklet. Yield was 312 ng/μl. Purity at 260/280 nm as measured on a NanVue spectrophotometer was 1.95.

Direct RT PCR was carried out in 96-well cluster plates using illustra Ready to Go-RT PCR beads 2.0 units of Taq polymerase, M-MuLV reverse transcriptase, 1.5 mM $MgCl_2$, 60 mM KCl, 10 mM Tris-HCL, stabilisers and 40 ng template RNA, prepared above with RT-PCR carried out in 50 μl volumes following the two-step method outlined in the instruction booklet.

Following addition of 200 μM dNTPs, reactions were Incubated at 42° C., 30 mins, and then followed by the addition of β-globin primer sequences.

β-globin primer sequences (Sigma Genosys) were as follows:

```
β-globin-exon I: Sequence (5' ... 3')
                                    (SEQ ID NO. 1)
    GGT GAA CGT GGA TGA AGT TG β-globin-exon III: Sequence (5' ... 3')
                                    (SEQ ID NO. 2)
    AGC ACA CAG ACC AGC ACG T
```

Figure 5:
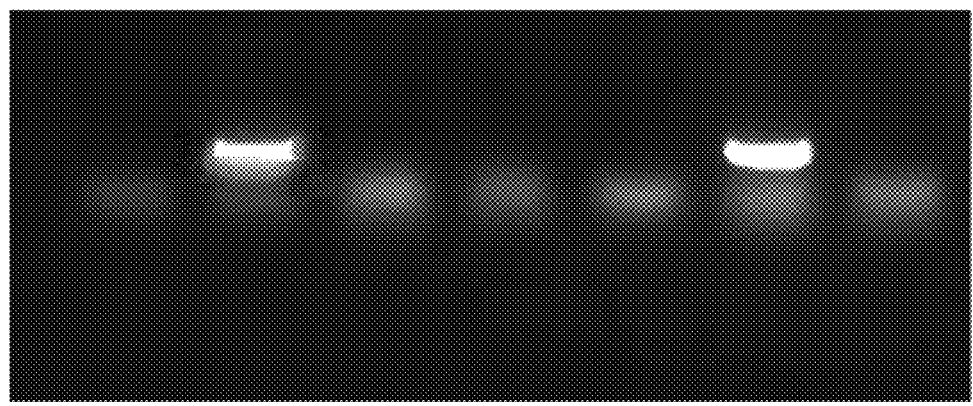

Thermocycling conditions were as follows:
94° C., 3 min
94° C. 30 secs
55° C., 1 min
72° C. 30 secs
72° C. 5 mins
42 cycles
4° C., for ever RN'ase free agarose gel electrophoresis (2% w/v) with 1 μl of 6× loading buffer, was carried out to analyse the products. Results are shown in FIG. 5. Lane 2 shows amplified β-globin gene fragment obtained from extracted RNA from the alginate coated matrix. These data shows that it is possible to extract and amplify RNA from the alginate coated matrix.

While preferred illustrative embodiments of the present invention are described, one skilled in the art will appreciate that the present invention can be practised by other than the described embodiments, which are presented for the purposes of illustration only and not by way of limitation. The present invention is limited only by the claims that follow.

What is claimed is:

1. A solid support for storing a biological material thereon, wherein the support comprises a cellulose matrix having sorbed thereto an alginate, a protein denaturing reagent, and a free radical trap.

2. A solid support for storing a biological material thereon, wherein the support comprises a cellulose matrix having sorbed thereto an alginate, a protein denaturing reagent, and a chelating agent.

3. The support of claim 1, further comprising a chaotrophic salt.

4. The support of claim 1, wherein the alginate has antimicrobial activity.

5. The support of claim 1, wherein the alginate is selected from the group consisting of calcium alginate, sodium alginate, potassium alginate, ammonium alginate, magnesium alginate, lithium alginate, and silver alginate.

6. A solid support for storing a biological material thereon, wherein the support comprises a cellulose matrix having sorbed thereto an alginate and a protein denaturing reagent, wherein the alginate is silver alginate.

7. The support of claim 1, wherein the matrix is a solid matrix.

8. The support of claim 1, wherein the biological material is stored thereon, and wherein the biological material is selected from the group consisting of a eukaryotic cell, a prokaryotic cell, and a prion cell.

9. The support of claim 1, wherein the biological material is stored thereon, and wherein the biological material is selected from the group consisting of a blood, a plasma, a saliva, a urine and a buccal cell.

10. The support of claim 1, wherein the biological material is stored thereon, and wherein the biological material comprises a biomolecule selected from the group consisting of a nucleic acid, a protein, a biopharmaceutical, and a polysaccharide.

11. A method for storing a biological material on a solid support comprising:
applying a biological material to a solid support comprising a cellulose matrix having sorbed thereto an alginate and a protein denaturing reagent, and
storing the biological material on the support without refrigeration.

12. The method of claim 11, wherein the biological material is stored on the support at a temperature ranging from 4° C. to 50° C.

13. The method of claim 11, wherein the sample is stored on the support for at least one day.

14. A method of detecting a biological material stored on a solid matrix support having sorbed thereto or incorporated therein an alginate and a protein denaturing reagent, the method comprising:
eluting the biological material from the support and detecting a presence, level, or both, of a biomolecule in the biological material.

15. The support of claim 1, further comprising a chelating agent.

16. The support of claim 2, further comprising a free radical trap and/or a chaotrophic salt.

17. The support of claim 2, wherein the alginate is selected from the group consisting of calcium alginate, sodium alginate, potassium alginate, ammonium alginate, magnesium alginate, lithium alginate, and silver alginate.

18. The support of claim 2, wherein the alginate is silver alginate.

19. The support of claim 2, wherein the matrix is a solid matrix.

20. The support of claim 6, further comprising a chelating agent, a free radical trap and/or a chaotrophic salt.

21. The support of claim 6, wherein the matrix is a solid matrix.

22. The method of claim 11, wherein the matrix has further sorbed thereto a chelating agent, a free radical trap and/or a chaotrophic salt.

23. The method of claim 11, wherein the alginate is selected from the group consisting of calcium alginate, sodium alginate, potassium alginate, ammonium alginate, magnesium alginate, lithium alginate, and silver alginate.

24. The method of claim 11, wherein the alginate is silver alginate.

25. The method of claim 14, wherein the matrix has further sorbed thereto a chelating agent, a free radical trap and/or a chaotrophic salt.

26. The method of claim 14, wherein the alginate is selected from the group consisting of calcium alginate, sodium alginate, potassium alginate, ammonium alginate, magnesium alginate, lithium alginate, and silver alginate.

27. The method of claim 14, wherein the alginate is silver alginate.

* * * * *